US005679771A

United States Patent [19]
Ballard et al.

[11] Patent Number: 5,679,771
[45] Date of Patent: Oct. 21, 1997

[54] METHOD FOR TREATING INTESTINAL DISEASES

[75] Inventors: Francis John Ballard, Glenalta; Leanna Christine Read, Kensington, both of Australia

[73] Assignee: Gropep Pty. Ltd., Adelaide, Australia

[21] Appl. No.: 321,585

[22] Filed: Oct. 11, 1994

Related U.S. Application Data

[63] Continuation of Ser. No. 854,983, filed as PCT/AU91/00031 Jan. 30, 1991, abandoned.

[30] Foreign Application Priority Data

Feb. 13, 1990 [AU] Australia ............... PJ 8586

[51] Int. Cl.⁶ ............................................. A61K 38/30
[52] U.S. Cl. ................... 530/324; 514/12; 530/399
[58] Field of Search ............... 514/12, 2; 530/324

[56] References Cited

U.S. PATENT DOCUMENTS

| | | | |
|---|---|---|---|
| 4,876,242 | 10/1989 | Applebaum et al. | 514/3 |
| 5,019,500 | 5/1991 | Ueda et al. | 435/69.1 |
| 5,028,531 | 7/1991 | Ueda et al. | 435/69.4 |
| 5,077,276 | 12/1991 | Ballard et al. | 514/12 |
| 5,128,320 | 7/1992 | Hahn . | |
| 5,164,370 | 11/1992 | Ballard et al. | 514/12 |

FOREIGN PATENT DOCUMENTS

| | | | |
|---|---|---|---|
| 21796/88 | 3/1989 | Australia | C12N 15/00 |
| 0158892 | 10/1985 | European Pat. Off. | C07K 7/10 |
| 0227619 | 7/1987 | European Pat. Off. | C07K 7/10 |
| 227619 | 7/1987 | European Pat. Off. . | |
| 266057 | 5/1988 | European Pat. Off. . | |
| 0309050 | 3/1989 | European Pat. Off. | C12N 15/00 |
| 307285 | 3/1989 | European Pat. Off. . | |
| 309050 | 3/1989 | European Pat. Off. . | |
| A10308386 | 3/1989 | European Pat. Off. . | |
| 0 379 338 | 7/1990 | European Pat. Off. | C07K 7/10 |
| WO 85/00831 | 2/1985 | WIPO . | |
| WO 87/01038 | 2/1987 | WIPO | A61K 37/24 |
| WO 89/05822 | 6/1989 | WIPO . | |
| WO 90/15142 | 12/1990 | WIPO . | |
| WO 92/03155 | 3/1992 | WIPO . | |

OTHER PUBLICATIONS

E. Rindernecht et al., *J. Biol. Chem.*, 253, 2769–2776 (1978).
R. B. Merrifield, *Angew. Chem. Int. Ed.*, 24, 799–810 (1985).
F. J. Ballard et al., *Biochem. and Biophys. Res. Commun.*, 149, 398–404.
Chemical Abstracts, vol. 104, No. 23, Abs. No. 203501c (1986), Blumberg et al.
Chemical Abstracts, vol. 106, No. 13, Abs. No. 96902b (1987), Carlsson–Skwirut et al.
Chemical Abstracts, vol. 108, No. 23, Abs. No. 198502e (1988), Francis et al.
Chemical Abstracts, vol. 108, No. 23, Abs. No. 202006r (1988), Dawe et al.
Chemical Abstracts, vol. 109, No. 3, Abs. No. 17150r (1988), Bayne et al.
Chemical Abstracts, vol. 109, No. 11, Abs. No. 86924h (1988), Cascieri et al.
C. Carlsson–Skwirut et al., *Biochem. Biophys. Acta*, 1011, 192–197 (1989).
M. Ross et al., *Biochem. J.*, 258, 267–272 (1989).
C. J. Bagley et al., *Biochem. J.*, 259, 665–671 (1989).
Chemical Abstracts vol. 97 No. 3 Nokihara, K. et al "Synthetic and Immunological Studies on C–domain of Insulin–like Growth Factor (IGF)".
Bagley et al., *Biochem. J.*, 259, 665–671 (1989).
Bayne et al., *Chemical Abstracts*, 109, Abs. No. 17150r (1988).
Ballard et al., *Biochem. and Biophys. Res. Commun.*, 149, 398–404 (1987).
Blumberg et al., *Chemical Abstracts*, 104, Abs. No. 203501c (1986).
Carlsson–Skwirut et al., *Biochim. Biophys. Acta*, 1011, 192–197 (1989).
Carlsson–Skwirut et al., *Chemical Abstracts*, 105, Abs. No. 36363w (1986).
Carlsson–Skwirut et al., *Chemical Abstracts*, 106, Abs. No. 96902b (1987).
Carlsson–Skwirut et al., *FEBS*, 201, 46–50 (1986).
Cascieri et al., *Chemical Abstracts*, 109, Abs. No. 86924h (1988).
Dawe et al., *Chemical Abstracts*, 108, Abs. No. 202006r (1988).
Fagerstedt et al., *ACTA Endoctrinol*, 103 (256), 216 (1983).
Francis et al., *Chemical Abstracts*, 108, Abs. No. 198502e (1988).
Giacobini et al., is believed to have been published in *Science* in either 1989 1990.
The Merck Index, 10th ed., No. 8560, 4354, 7685, 4330, 9229 and 5288 at pages 1246, 645, 1121, 641, 1344, and 782, respectively (1983).
Merrifield, *Angew. Chem. Int. Ed. Engl.*, 24, 799–810 (1985).
Nokihara et al., *Chemical Abstracts*, 97, Abs. No. 24215c (1982).
Rinderknecht et al., *J. Biol. Chem.*, 253, 2769–2776 (1978).
Ross et al., *Biochem J.*, 258, 267–272 (1989).
Rudinger, *Peptide Hormones*, (Parsons Ed.), University Park Press, 1–5 (1976).
Sara et al., *Chemical Abstracts*, 105, Abs. No. 73328j (1986).
Sara et al., *Proc. Natl. Acad. Sci. USA*, 78, 3175–3179 (1981).

(List continued on next page.)

Primary Examiner—Cecilia J. Tsang
Assistant Examiner—David Lukton
Attorney, Agent, or Firm—Merchant, Gould, Smith, Edell, Welter & Schmidt, P.A.

[57] ABSTRACT

A method for the treatment of disorders in gut function in animals including humans, which method includes administering to a patient to be treated an effective amount of a mammalian insulin-like growth factor-I (IGF-I) or a peptide analogue thereof.

14 Claims, 1 Drawing Sheet

OTHER PUBLICATIONS

Sara et al., *Proc. Natl. Acad. Sci. USA*, 83, 4904–4907 (1986).

Svoboda et al., *Biochemistry*, 19, 790–797 (1980).

Rudinger, *Pept. de Hormones*, Parsons (Ed.), U Park Press, Baltimore (1976).

Sara et al., *Proc. Nat'l Acad. Sci., USA*, 78, 3175–3179 (1981).

*Chemical Abstracts*, vol. 97, No. 3, Abs. No. 24215c (1982) Nokihara et al.

Fagerstedt et al., *ACTA Endocrinol*, 103, (256), 216 (1983).

Sara et al., *Proc. Nat'l Acad., USA*, 83, 4900–4907 (1986).

Carlsson–Skwirut et al., *FEBS*, 201, No. 1, 46–50 (1986).

*Chemical Abstracts*, vol. 105, No. 5, Abs. No. 36363w (1986) Carlsson-Skwirut et al.

*Chemical Abstracts*, vol. 105, No. 9, Abs. No. 73328j (1986) Sara et al.

Ballard et al; Modern concepts of Insulin–like Growth Facotrs (E.M. Spencer, Ed.) Elsevier, pp. 617–627 (1991).

Read et al; Modern concepts of Insulin–like Growth Factors (E.M. Spencer, Ed.) Elsevier, pp. 225–234 (1991).

Tomas et al; Biochem. J. 282, 91–97 (1992).

Read et al; Proc. Nutr. Soc. New Zealand 17, 136–142 (1992).

Read et al; J. Endocrinol. 133, 421–431 (1992).

Ballard et al; Growth Regul. 3, 40–44 (1993).

Ballard et al; Proceedings of the 9th International Congress of Endocrinology, in press.

Ballard et al; Growth and Sexual Development (C. Cowell, K. Ho & G. Werther, Eds.) Harwood, in press.

Tomas et al; Biochem. J. in press.

Tomas et al; "Anabolic effects of insulin–like growth factor–1 (IGF–I) and an IGF–I variant in normal female rats".

Francis et al; J. Mol. Endocrin. 8, 213–223 (1992).

Exhibit A –"Henderson's Dictionary of Biological Terms", 10th Edition, 1989.

Vize et al; FEB 04467, vol. 213, No.1, 155–158; Mar. 1987.

Sproat et al; Nucleic Acids Research, vol. 13, No. 8, 1985, pp. 2959–2977.

Kadonaga et al; Cell, vol. 51, 1979–1090, Dec. 24, 1987.

D'Andrea et al; Nucleic Acids Research, vol. 9, No. 13, 1981.

Brosius et a., *J. biol. Chem.*, 260, 3539–3541 (1985).

Carter et al., *Proteins: Structure, Function, and Genetics*, 6, 240–248, (1989).

Amman et al., *Gene*, 40, 183–190 (1985).

Messing, *Recomb. DNA Tech. Bull.*, 2 43–48 (1979).

Francis et al., *Biochem. J.*, 233, 207–213 (1986).

Rinderknecht et al., *FEBS Lett.*, 89, 283–286 (1978).

Ballard et al., *Aust. J. Agric. Res.*, 44, 1–11 (1992).

Read et al., "The Gastrointestinal Tract is one of the Most Responsive Target Tissues for IGF–I and it Potent Analogs", *Modern Concepts of Insulin–Like Growth Factors*, Elsevier Science Publishing Co., Inc. E.M. Spencer (Editor), 225–234 (1991).

Read et al., "The Gastrointestinal Tract: A Most Sensitive Target for IGF–I" *Proc. Nutr. Soc. of New Zealand*, 17, 136–142 (1992).

Read et al., "Insulin–Like Growth Factor–I and its N–Terminal Modified Analogues Induce Marked Gut Growth in Dexamethasone–Treated Rats", *J. Endocrinology*, 133, 421–431 (Jun., 1992).

Tomas et al., "Insulin–Like Growth Factor–I (IGF–I) and Especially IGF–I Variants are Anabolic in Dexamethasone–Treated Rats", *Biochem. J.*, 282, 91–97 (Feb., 1992).

Werner et al., "Development Regulation of the Rat Insulin–Like Growth Factor I Receptor Gene", *Proc. Natl. Acad. Sci. USA*, 86, 7451–7455 (Oct., 1989).

Young et al., "Insulin–Like Growth Factors and the Developing and Mature Rat Small Intestine: Receptors and Biological Actions", *Digestion*, 46, 240–252 (1990).

Behringer et al., "Expression of Insulin–Like Growth Factor I Stimulates Normal Somatic Growth in Growth Hormone–Deficient Transgenic Mice", *Endocrinology*, 127, 1033–1040 (Sep., 1990).

D'Ercole et al., "Tissue and Plasma Somatomedin–C/Insulin–Like Growth Factor I Concentrations in the Human Fetus During the First Half of Gestation", *Pediatr. Res.*, 20, 253–355 (Mar., 1986).

Gillespie et al., "Enhanced Potency of Truncated Insulin–Like Growth Factor–I (des(1–3)IGF–I) Relative to IGF–I in lit/lit Mice", *J. Endocrinology*, 127, 401–405 (Dec., 1990).

Hansson et al., "Immunohistochemical Localization of Insulin–Like Growth Factor I in the Adult Rat", *Histochemistry*, 89, 403–410 (1988).

Laburthe et al., "Receptors for Insulin–Like Growth Factors I and II in Rat Gastrointestinal Epithelium", *Am. Physiol. Soc.*, 254, G457–G462 (Mar., 1988).

Lemmey et al., "IGF–I and the Truncated Analogue des–(1–3)IGF–I Enhance Growth in Rats After Gut Resection", *Am. Physiol. Soc.*, 260, E213–E219 (Feb., 1991).

Lowe Jr. et al., "Regulation by Fasting of Rat Insulin–Like Growth Factor I and its Receptor; Effects on Gene Expression and Binding", *J. Clin. Invest.*, 84, 619–626 (Aug., 1989).

Lund et al., "Somatomedine–C/Insulin–Like Growth Factor–I and Insulin–Like Growth Factor–II mRNAs in Rat Fetal and Adult Tissues", *J. Biol. Chem.*, 261, 14539–14544 (Nov., 1986).

Pillion et al., "Receptors for IGF–I, but not for IGF–II, on Proximal Colon Epithelial Cell Apical Membranes", *Am. Physiol. Soc.*, 257, E27–E34 (Jul., 1989).

Amann et al., "'ATG Vectors'for Regulated High–Level Expression of Cloned Genes in *Escherichia coli*", *Gene*, 40, 183–190 (1985).

D'Andrea et al., *Nucleic Acids Research*, 9, 3119–3128 (1981).

Bagley et al., "A Key Functional Role for the Insulin–Like Growth Factor I N–Terminal Pentapeptide", *Biochem. J.*, 259, 665–671 (1989).

Ballard et al., "Binding Properties and Biological Potencies of Insulin–Like Growth Factors in L6 Myoblasts", *Biochem J.*, 233, 223–230 (1986).

Ballard et al., "Natural and Synthetic Forms of Insulin–Like Growth Factor–I (IGF–I) and the Potent Derivative, Destripeptide IGF–I: Biological Activities and Receptor Binding", *Biochem. and Biophys. Res. Commun.*, 149, 398–404 (1987).

Ballard et al., "Effects of IGF–I and IGF Analogs on Growth During Catabolic States in Rats", *Modern Concepts of Insulin–Like Growth Factors*, (E.M. Spencer, Ed.) 617–627 (1991).

Ballard et al., "Modification of Animal Growth With Growth Hormone and Insulin–Like Growth Factors", *Aust. J. Agric. Res.*, 44, 1–11 (1992).

Ballard et al., "Effects of Interactions Between IGFBPs and IGFs on the Plasma Clearance and in vivo Biological Activities of IGFs and IGF Analogs", *Growth Regulation*, 3, 40–44 (1993).

Ballard et al., "Anticatabolic Effects of IGF–I", *Proceedings of the 9th International Congress of Endocrinology*, in press.

Ballard et al., "Anabolic Effects of IGF", *Cooperative Research Centre for Tissue Growth and Repair*, (1993).

Bayne et al., "Expression of a Synthetic Gene Encoding Human Insulin–Like Growth Factor I in Cultured Mouse Fibroblasts", *Proc. Natl. Acad. Sci. USA*, 84, 2638–2642 (1987).

Bayne et al., "Structural Analogs of Human Insulin–Like Growth Factor I With Reduced Affinity for Serum Binding Proteins and the Type 2 Insulin–Like Growth Factor Receptor", *Chemical Abstracts*, 109, 68, Abs. No. 17150r (1988).

Blumberg et al., "Removable N–Terminal Amino Acid Residues From Eukaryotic Polypeptide Analogs and Polypeptides", *Chemical Abstracts*, 104, Abs. No. 203501c (1986).

Brosius et al., "Spacing of the −10 and −35 Regions in the tac Promoter: Effect on its in vivo Activity", *J. Biol. Chem.*, 260, 3539–3541 (1985).

Carlsson–Skwirut et al., "Isolation and Characterization of Variant IGF–I as Well as IGF–2 From Adult Human Brain", *FEBS Letters*, 201, 46–50 (1986).

Carlsson–Skwirut et al., "Circulating Forms of Human Fetal Somatomedin", *Chemical Abstracts*, 106, 156–157, Abs. No. 96902b (1987).

Carlsson–Skwirut et al., "Isolation and Characterization of Variant IGF–I as Well as IGF–2 From Adult Human Brain", *Chemical Abstracts*, 105, 147, Abs. No. 36363w (1986).

Carlsson–Skwirut et al., "A Comparison of the Biological Activity of the Recombinant Intact and Truncated Insulin–Like Growth Factor–I", *Biochim. Biophys. Acta*, 1011, 192–197 (1989).

Carter et al., "Engineering Subtilisin BPN' for Site–Specific Porteolysis", *Proteins: Structure, Function, and Genetics*, 6, 240–248 (1989).

Cascieri et al., "Inability of a Mouse Cell Line Transformed to Produce Biologically Active Recombinant Human Insulin–Like Growth Factor–I (IGF–I) to Respond to Exogenously Added IGF–I", *Endocrinology*, 122, 1314–1320 (1988).

Cascieri et al., "Serum Half–Life and Biological Activity of Mutants of Human Insulin–Like Growth Factor I Which do not Bind to Serum Binding Proteins", *Chemical Abstracts*, 109, 146, Abs. No. 86924h (1988).

Dawe et al., "Purification, Partial Sequences and Properties of Chicken Insulin–Like Growth Factors", *Chemical Abstracts*, 108, 421, Abs. No. 202006r (1988).

Fagerstedt et al., "Purification of Human Fetal Somatomedin", *ACTA Endocrinol.*, 103, 216 (1983).

Francis et al., "Purification and Partial Sequence Analysis of Insulin–Like Growth Factor–1 from Bovine Colostrum", *Biochem J.*, 233, 207–213 (1986).

Francis et al., "Insulin–Like Growth Factors 1 and 2 in Bovine Colostrum. Sequences and Biological Activities Compared with Those of a Potent Truncated Form", *Chemical Abstracts*, 108, 82–83, Abs. No. 198502e (1988).

Francis et al., "Novel Recombinant Fusion Protein Analoques of Insulin–Like Growth Factor (IGF)–I Indicate the Relative Importance of IGF–Binding Protein and Receptor Binding for Enhanced Biological Potency", *J. Mol. Endocrin.*, 8, 213–223 (1992).

Giacobini et al., "Truncated IGF–1 Exerts Trophic Effects on Fetal Brain Tissue Grafts", *Science* (1990).

Giacobini et al., "Acidic and Basic Fibroblast Growth Factors Augment Growth of Fetal Brain Tissue Grafts", *Exp. Brain. Res.*, 86, 73–81 (1991).

*Henderson's Dictionary of Biological Terms*, 10th Edition (1989).

Humbel, "Insulin–Like Growth Factors I and II", *Eur. J. Biochem.*, 190, 445–462 (1990).

Iwai et al., "Deoxyribonucleic Acids and Related Compounds. XXII. Synthesis of Genes for Human Nerve Growth Factor and its Fused Protein", *Chem. Pharm. Bull.*, 34, 4724–4730 (1986).

Kadonaga et al., "Isolation of cDNA Encoding Transcription Factor Sp1 and Functional Analysis of the DNA Binding Domain", *Cell*, 51, 1079–1090 (1987).

Kirschner et al., "Somatomedin–C Levels in Growth–Impaired children and Adolescents with Chronic Inflammatory Bowel Disease", *Gastroenterology*, 91, 830–836 (1986).

Kirschner et al., "Failure of Somatomedin–C (SM–C) to Increase After Treatment of Childhood Crohn's Disease Distinguishes Disease–Related Growth Failure From Hypopituitarism", (Abstract) *Gastroenterology*, 92, 1468 (1987).

Li et al., "Total Synthesis of Insulin–Like Growth Factor I (Somatomedin C)" *Proc. Nat'l. Acad. Sci. USA*, 80, 2216–2220 (1983).

Lund et al., "Somatomedin–C/Insulin–Like Growth Factor–I and Insulin–Like Growth Factor–II mRNAs in Rat Fetal and Adult Tissues", *J. Biol. Chem.*, 261, 14539–14544 (1986).

Martin et al., "Insulin–Like Growth Factor–Binding Protein From Human Plasma", *J. Biol. Chem.*, 261, 8754–8760 (1986).

Merrifield, "Solid Phase Synthesis (Nobel Lecture)", *Angew. Chem. Int. Ed. Engl.*, 24, 799–810 (1985).

Merck Index, 10th ed., No. 8560, 4354, 7685, 9330, 9229 and 5788, p. 1246, 645, 1121, 641, 1344 and 782 (1983).

Messing, "A Multipurpose Cloning system Based on the Single–Stranded DNA Bacteriophage M13", *Recomb. DNA Tech. Bull.*, 2, 43–48 (1979).

Misoka et al., "Overproduction of Human Insulin–Like Growth Factor–II in *Escherichia coli*", *Biotechnology Letters*, 11, 839–844 (1989).

Moore et al., "Re–Routing of a Secretory Protein by Fusion with Human Growth Hormone Sequences", *Nature*, 321, 443–446 (1986).

Nishikawa et al., "Efficient Cleavage by Alpha–Thrombin of a Recombinant Fused Protein Which Contains Insulin–Like Growth Factor I", *Protein Engineering*, 1, 487–492 (1987).

Nokihara et al., "Synthetic and Immunological Studies on C–domain of Insulin–like Growth Factor (IGF)", *Chemical Abstracts*, 97, 756, Abs. No. 24215c (1982).

Olson et al., "Grafts, Growth Factors and Grafts that Make Growth Factors", *Prog. Brain Res.*, 82, 55–66 (1990).

Read et al., "The Gastrointestinal Tract is One of the Most Responsive Target Issues for IGF–I and its Potent Analogs", *Modern Concepts of Insulin–Like Growth Factors*, (E.M. Spencer, Ed.) 225–234 (1991).

Rinderknecht et al., "Primary Structure of Human Insulin–Like Growth Factor II", *FEBS Lett.*, 89, 283–286 (1978).

Rindernecht et al., "The Amino Acid Sequence of Human Insulin–Like Growth Factor I and its Structural Homology With Proinsulin", *J. Biol. Chem.*, 253, 2769–2776 (1978).

Rosenthal et al., "Growth Failure and Inflammatory Bowel Disease: Approach to Treatment of a Complicated Adolescent Problem", *Pediatrics*, 72, 481–490 (Oct., 1983).

Ross et al., "Insulin–Like Growth Factor (IGF)–Binding Proteins Inhibit the Biological Activities of IGF–1 and IGF–2 but not des–(1–3)–IGF–1", *Biochem. J.*, 258, 267–272 (1989).

Rudinger et al., "Characteristics of the Amino Acids as Components of a Peptide Hormone Sequence", *Peptide Hormones* (Parsons, ed.), U. Park Press Baltimore 1–7, (1976).

Sara et al., "Human Embryonic Somatomedin", *Proc. Natl. Acad. Sci. USA*, 78, 3175–3179 (1981).

Sara et al., "Characterization of Somatomedins From Human Fetal Brain: Identification of a Variant Form of Insulin–Like Growth Factor I", *Proc. Natl. Acad. Sci. USA*, 83, 4904–4907 (1986).

Sara et al., "Characterization of Somatomedins From Human Fetal Brain: Identification of a Variant Form of Insulin–Like Growth Factor I", *Chemical Abstracts*, 105, Abs. No. 73328j (1986).

Sarin et al., "Quantitative Monitoring of Solid–Phase Peptide Suynthesis by the Ninhydrin Reaction", *Anal. Biochem.*, 117, 147–157 (1981).

Sproat et al., "Chemical Synthesis of a Gene for Somatomedin C", *Nucleic Acids Research*, 13, 2959–2977 (1985).

Svoboda et al., "Purification of Somatomedin–C From Human Plasma: Chemical and Biological Properties, Partial Sequence Analysis, and Relationship to Other Somatomedins", *Biochemistry*, 19, 730–797 (1980).

Tavakkol et al., "Porcine Insulin–Like Growth Factor–I (pIGF–I): Complementary Deoxyribonucleic Acid Cloning and Uterine Expression of Messenger Ribonucleic Acid Encoding Evolutionarily Conserved IGF–I Peptides", *Molecular Endrocrinology*, 2, 674–681 (1988).

Tomas et al., "Insulin–Like Growth Factor–I and More Potent Variants Restore Growth of Diabetic Rats Without Inducing all Characteristics Insulin Effects", *Biochem J.*, 291, 1–6 (1993).

Tomas et al., "Anabolic Effects of Insulin–Like Growth Factor–I (IGF–I) and an IGF–I Variant in Normal Female Rats", *Cooperative Research Centre for Tissue Growth and Repair*, 1–14, (1993).

Vize et al., "Spacer Alterations Which Increase the Expression of Porcine Growth Hormone in *E. coli*", *FEB Letters*, 213, 155–158 (Mar. 1987).

Vize et al., "Isolation and Characterization of the Porcine Growth Hormone Gene", *Gene*, 55, 339–344 (1987).

Werner et al., "Developmental Regulation of the Rat Insulin–Like Growth Factor I Receptor Gene", *Proc. Natl. Acad. Sci. USA*, 86, 7451–7455 (Oct., 1989).

F.J. Ballard, *Biochem. J.*, 233, 223–230 (1986).

C. Carlsson–Skwirut et al., *Chem. Abstr.*, 105, 147, Abstract No. 105:36363w (1986).

G.L. Francis et al., *Biochem. J.*, 233, 207–213 (1986).

C.H. Li et al., *Proc. Natl'l. Acad. Sci. USA*, 80, 2216–2220 (1983).

J.L. Martin et al., *J. Biol. Chem.*, 261, 8754–8760 (1986).

V.R. Sara et al., *Chem. Abstr.*, 105, Abstract No. 105:73328j (1986).

V.K. Sarin, et al., *Anal. Biochem.*, 17, 147–157 (1981).

M.M.J. Giacobini et al., *Exp. Brain Res.*, 86, 73–81 (1991).

L. Olson et al., *Prog. Brain Res.*, 82, 55–66 (1990).

Bayne et al., *Chemical Abstracts*, vol. 109, No. 3, Abs. No. 17150r (1988).

Blumberg et al., *Chemical Abstracts*, vol. 104, No. 23, Abs. No. 203501c (1986).

C. Carlsson–Skwirut et al., *FEBS*, 201, No. 1, 46–50 (1986).

C. Carlsson–Skwirut et al., *Chemical Abstracts*, vol. 106, No. 13, Abs. No. 96902b (1987).

Cascieri et al., *Chemical Abstracts*, vol. 109, No. 11, Abs. No. 86924h (1988).

Dawe et al., *Chemical Abstracts*, vol. 108, No. 23, Abs. No. 202006r (1988).

Fagerstedt et al., *Acta Endorcrinol.*, 103, 216 (1983).

Francis et al., *Chemical Abstracts*, vol. 108, No. 23, Abs. No. 198502e (1988).

M. M. J. Giacobini et al., is believed to have been published in *Science* in either 1989 or 1990.

*The Merck Index*, *10th ed.*, 8560, 4354, 7685, 4330, 5288, and 9229, p. 1246, 645, 1121, 641, 1344, 782 (1983).

Nokihara K. et al., *Chemical Abstracts*, vol. 97, No. 3, Abs. No. 24215c (1982) "Synthetic and Immunological Studies on C–domain of Insulin–like Growth Factor (IGF)".

E. Rinderknecht et al., *J. Biol. Chem.*, 253, 2769–2776 (1978).

Rudinger, *Peptide Hormones Parsons (ed.)*, U Park Press, Baltimore, pp. 1–7 (1976).

Sara et al., *Proc. Natl. Acad. Sci.: USA* 78, No. 5, 3175–3179 (1981).

Sara et al., *Proc. Natl. Acad. Sci.: USA*, 83, 4904–4907 (1986).

A. Tavakkol, et al., *Molecular Endrocrinology*, 2, 674–681 (1988).

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

Val Leu Cys
1

( 2 ) INFORMATION FOR SEQ ID NO:2:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

Arg Leu Cys
1

( 2 ) INFORMATION FOR SEQ ID NO:3:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:3:

Gly Leu Cys
1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:4:

Gly Thr Leu Cys
1

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:5:

Gly Pro Arg Thr Leu Cys
1                5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:6:

Gly Pro Gly Arg Leu Cys
1                5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:7:

Gly Pro Gly Gly Leu Cys
1               5

(2) INFORMATION FOR SEQ ID NO:8:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:8:

Gly Pro Gly Thr Leu Cys
1               5

(2) INFORMATION FOR SEQ ID NO:9:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:9:

Gly Pro Gln Thr Leu Cys
1               5

(2) INFORMATION FOR SEQ ID NO:10:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal -continued (vi) ORIGINAL SOURCE:

(xi) SEQUENCE DESCRIPTION: SEQ ID NO:10:

```
Gly  Pro  Lys  Thr  Leu  Cys
 1                 5
```

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:11:

```
Gly  Pro  Leu  Thr  Leu  Cys
 1                 5
```

(2) INFORMATION FOR SEQ ID NO:12:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:12:

```
Met  Phe  Pro  Ala  Met  Pro  Leu  Ser  Ser  Leu  Phe  Val  Asn  Gly  Pro  Arg
 1                  5                         10                      15
Thr  Leu  Cys  Gly  Ala  Glu  Leu  Val  Asp  Ala  Leu  Gln  Phe  Val  Cys  Gly
                20                      25                      30
Asp  Arg  Gly  Phe  Tyr  Phe  Asn  Lys  Pro  Thr  Gly  Tyr  Gly  Ser  Ser  Ser
           35                      40                      45
Arg  Arg  Ala  Pro  Gln  Thr  Gly  Ile  Val  Asp  Glu  Cys  Cys  Phe  Arg  Ser
     50                      55                      60
Cys  Asp  Leu  Arg  Arg  Leu  Glu  Met  Tyr  Cys  Ala  Pro  Leu  Lys  Pro  Ala
 65                      70                      75                      80
Lys  Ser  Ala
```

METHOD FOR TREATING INTESTINAL DISEASES

This is a continuation of application Ser. No. 07/854,983, filed as PCT/AU91/00031 Jan. 30, 1991, now abandoned.

BACKGROUND OF THE INVENTION

This invention relates to insulin-like growth factor-I (IGF-I) and its analogues. More particularly, the invention relates to the use of IGF-I and its analogues to treat disorders in gut function, e.g. relating to the effects of intestinal diseases.

IGF-I is a small protein that has been shown to stimulate the growth of cells in culture. Animal growth is also stimulated in pituitary-deficient, normal and catabolic states. Kidney function is also improved. These studies have led to the interpretation that IGF-I may be usefully applied in humans:

(1) to treat growth hormone deficiencies;

(2) to suppress the loss of body protein in catabolic states following burns, infection or other trauma; and (3) as a treatment for patients suffering from renal diseases.

A number of human diseases result either in the subject having a lesser amount of gut tissue than required for normal digestion or absorption, or alternatively a diseased but normal-length gut in which digestion or absorption is impaired. Examples of human diseases that fit these two categories include short-gut syndrome, chronic ulcerative gut diseases, inflammatory gut diseases such as colitis and Crohn's disease, and necrotising enterocolitis in infants.

IGF-I is not known in the prior art to increase the growth or function of the cell types that comprise the abdominal gut, viz the stomach, duodenum, jejunum, ileum, cecum and colon. It is these regions of the gut that are affected in the diseases described above. Gut tissues do contain receptors for IGF-I (for example see: M. Laburthe et al, Am. J. Physiol. 254, G457, 1988; D. J. Pillion et al., Am. J. Physiol. 257, E27, 1989; H. Werner et al, Proc. Natl. Acad. Sci. USA 86, 7451, 1989), and are known under certain conditions to synthesise IGF-I or IGF-I messenger RNA (for example see: P. K. Lund et al., J. Biol. Chem. 251, 14539, 1986; A. J. D'Ercole et al., Pediatr. Res. 20, 253, 1986; H.-A. Hansson et al., Histochemistry 89, 403, 1988; W. L. Lowe, Jr., J. Clin. Invest. 84, 619, 1989).

IGF-I has previously been administered to dwarf mice, hypophysectomized rats, diabetic rats, starved mice and rats, normal rats, mini poodles and normal human subjects. The levels of IGF-I have also been increased by insertion of an IGF-I-expressing transgene in mice. In most of these studies IGF-I treatment has led to an increase in body growth. It has been noted that an undesirable side effect of high doses of IGF-I is hypoglycemia. However, in none of the reported studies was there any indication of an IGF-I effect on the abdominal gut. For example in one investigation where over expression of IGF-I was produced by transgenesis and led to substantial body growth in transgenic mice, the fractional weight of the duodenum was the same as in IGF-deficient animals (R. R. Behringer et al., Endocrinology 127, 1033, 1990). In another study the administration of low doses of IGF-I to suckling rats did not alter the weights of gastrointestinal organs (G. P. Young et al., Digestion 46S2, 240, 1990). In particular, there exists no prior report on the increase of gut weight following IGF-I administration.

It is accordingly an object of the present invention to overcome or at least alleviate, one or more of the difficulties related to the prior art.

SUMMARY OF THE INVENTION

The first aspect of the present method concerns the treatment of animals, including humans, with disorders in gut function by using mammalian, preferably human IGF-I.

Accordingly in a first aspect of the present invention there is provided a method for the treatment of disorders in gut function in animals, including humans, which method includes administering to a patient to be treated an effective amount of mammalian insulin-like growth factor-1 (IGF-I) or a peptide analogue thereof.

DETAILED DESCRIPTION OF THE INVENTION

Figure 1:
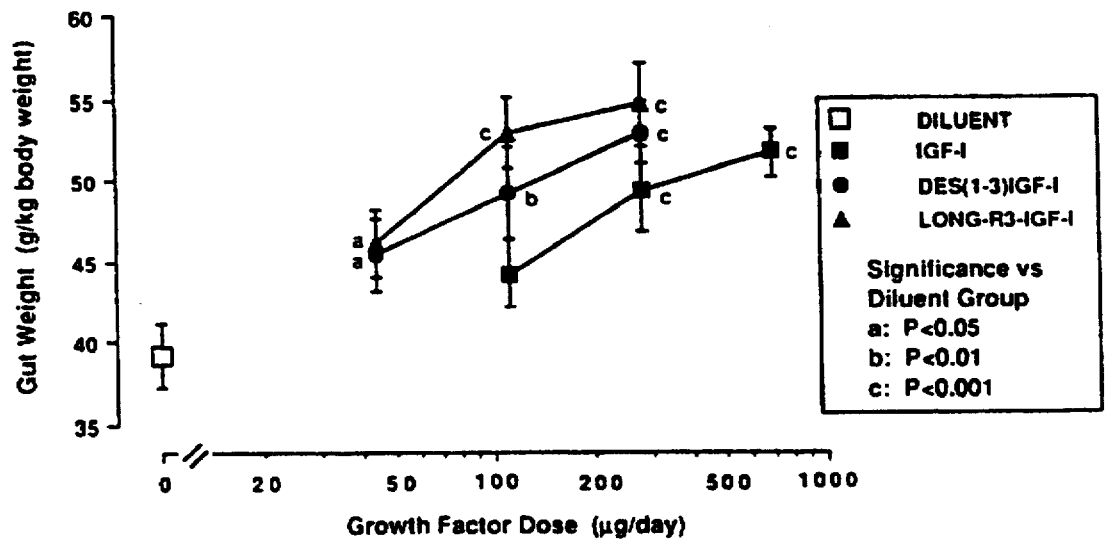
FIG. 1 illustrates the effect of IGF-I, des(1–3)IGF-I and $LR^3$ on total gut weight in dexamethasone-treated rats. Letters indicate statistical significance (ANOVA) from diluent group: (a) $P<0.05$; (b) $P<0.01$; (c) $P<0.001$.

By the term "disorders in gut function", as used herein, we mean disorders in one or more of the stomach, duodenum, jejunum plus ileum, and colon, resulting in reduced digestion or absorption by the gut. Such disorders may relate to intestinal diseases and/or the surgical treatment of the intestine. Thus where reference is made herein in general terms to the treatment of intestinal diseases, it is to be understood that we include the treatment of non-diseased intestines, part of which have been surgically removed and where increased growth of the residual intestine may be advantageous.

The term "peptide analogue", as used herein, is as defined as one or more of the peptide analogues referred to in applicant's International Patent Applications PCT/AU86/00246 and PCT/AU88/00485, or fusion proteins derived therefrom as described in International Patent Application PCT/AU90/00210, referred to above, the entire disclosures of which are incorporated herein by reference. PCT/AU86/00246; PCT/AU88/00485; and PCT/AU90/00210 correspond, respectively, to U.S. Pat. Nos. 5,077,776; 5,164,370; and U.S. Pat. No. 5,330,971, the disclosures of which are incorporated herein by reference.

An effective amount of mammalian IGF-I or an analogue of IGF-I is defined as that needed to increase the weight of gut tissue by more than approximately 20% above the weight of gut tissue prior to treatment.

Surprisingly IGF-I and its analogues have now been found by the applicants to increase the weight of the stomach, duodenum, jejunum plus ileum, and colon as well as the total gut weight. Of particular significance is the fact that these effects on growth have been found to occur in animals under a range of conditions, including (a) in animals in which gut function had previously been markedly compromised by the surgical removal of a substantial portion of the jejunum plus ileum (b) animals to which glucocorticoids have been administered in order to produce a catabolic state (c) animals in which diabetes had been induced by the drug streptozotocin, a condition that led to gut growth so that the effects of IGF-I were above an already-stimulated growth state, and (d) animals which had compromised kidney function.

Since glucocorticoids are administered to humans as a current treatment for the inflammation that characterizes several gut diseases, the present discovery that gut growth can be partially restored by IGF-I or its analogues even in the presence of glucocorticoids is both surprising and advantageous.

In a preferred aspect of the present invention a peptide analogue to mammalian, preferably human, IGF-I is administered. Preferably the peptide analogue is an analogue wherein from 1 to 5 amino acid residues are absent from the N-terminal of mammalian IGF-I. Preferably 3 amino acid residues are absent therefrom. Such peptide analogue has been designated des(1-3)IGF-I.

Alternatively the peptide analogue may be an analogue wherein at least the glutamic acid residue is absent at position 3 from the N-terminal of mammalian IGF-I, and optionally replaced by a different amino acid residue. Preferably the analogue is one wherein the glutamic acid residue is replaced by an arginine residue.

More preferably the peptide analogue has an N-terminal sequence selected from
Val-Leu-Cys-(SEQ.ID NO:1)
Arg-Leu-Cys-(SEQ.ID NO:2)
Gly-Leu-Cys-(SEQ.ID NO:3)
Gly-Thr-Leu-Cys-(SEQ.ID NO:4)
Gly-Pro-Arg-Thr-Leu-Cys-(SEQ.ID NO:5)
Gly-Pro-Gly-Arg-Leu-Cys-(SEQ.ID NO:6)
Gly-Pro-Gly-Gly-Leu-Cys-(SEQ.ID NO:7)
Gly-Pro-Gly-Thr-Leu-Cys-(SEQ.ID NO:8)
Gly-Pro-Gln-Thr-Leu-Cys-(SEQ.ID NO:9)
Gly-Pro-Lys-Thr-Leu-Cys-(SEQ.ID NO:10)
Gly-Pro-Leu-Thr-Leu-Cys-(SEQ.ID NO:11) with the Cys residue shown being that normally at position 6 from the N-terminal.

In a further alternative aspect, the peptide analogue is a fusion protein including
a first amino acid sequence including approximately the first 100 N-terminal amino acids of methionine porcine growth hormone, or a fragment thereof; and
a second amino acid sequence of mammalian insulin-like growth factor-1, or an analogue thereof, joined to the C-terminal of the first amino acid sequence.

Preferably the first amino acid sequence includes approximately the first 46, more preferably the first 11, N-terminal amino acids of methionine porcine growth hormone, or a fragment thereof.

The IGF-I analogues include des(1-3)IGF-I, specified in the co-owned International application PCT/AU86/00246, which specification is included herein by reference and had been shown to increase the growth of cultured cells at lower dose rates than required for IGF-I. In the development of the present invention, des (1-3)IGF-I has surprisingly been shown to show this increased potency in vivo, in the treatment of disorders in gut function, since lower concentrations of the analogue than of IGF-I itself produce comparable increases in the growth of gut tissue.

The IGF-I analogues also include a fusion protein MpGH (11)VN/R$^3$IGF-I (SEQ.ID NO:12) (abbreviated to LR$^3$ or long-R3-IG F-1), specified as Example 13 in the co-owned International Application PCT/AU90/00210, which specification is included herein by reference, and had been shown to increase the growth of cultured cells at lower dose rates than required for IGF-I. In the present invention, LR$^3$ has also surprisingly been shown to show increased potency in the treatment of disorders in gut function, since lower concentrations of the analogue than of IGF-I itself produce comparable increases in the growth of gut tissue.

Although the method in particular applies to the treatment of human subjects with IGF-I or an analogue of IGF-I, it can also be applied veterinarily to animals with intestinal diseases.

Accordingly, in a further aspect, the present invention provides a pharmaceutical or veterinary composition for the treatment of disorders in gut function including:
(a) an effective amount of a mammalian, preferably human, IGF-I or peptide analogue thereof; and
(b) a pharmaceutically or veterinarily acceptable diluent, carrier or excipient therefor.

In a preferred form, the present invention provides a pharmaceutical or veterinary composition wherein the IGF-I or the analogue of IGF-I is present in amounts sufficient to provide a dose rate of approximately 10 to 2000, preferably 100 to 1000 micrograms/kg body weight/day.

In a further preferred aspect of the present invention, there is provided a method for the treatment of disorders in gut function which method includes administering to a patient to be treated a pharmaceutical or veterinary composition including
(a) an effective amount of a mammalian, preferably human, IGF-I or peptide analogue thereof, and
(b) a pharmaceutically or veterinarily acceptable diluent, carrier or excipient therefor;
intravenously, subcutaneously, intramuscularly or enterally at a dose rate of approximately 10 to 2000, preferably 100 to 1000 micrograms/kg body weight/day. Treatment may continue for a period of approximately 1 to 60 days, preferably approximately 5 to 30 days.

The dose rate, dose intervals and treatment period may be adjusted to the degree of intestinal disease and the route of administration. Caution should be taken that blood glucose is monitored so that hypoglycemia can be prevented.

The dose rates and intervals for the administration of des(1-3)IGF-I and related analogues may be set at levels proportionally adjusted to the relative potency of the analogue to that of IGF-I itself. For example the levels for des(1-3)IGF-I or LR$^3$ will be proportionally less than for the full IGF-I peptide in accordance with the increased potency of des(1-3)IGF-I or LR$^3$. Dose rates of 50 to 500 micrograms of des(1-3) IGF-I LR$^3$/kg body weight/day are preferred.

In a still further aspect of the present invention there is provided the use of a mammalian insulin-like growth factor-1 (IGF-I) or a peptide analogue thereof for the manufacture of a pharmaceutical or veterinary preparation for the treatment of disorders in gut function.

The pharmaceutical or veterinary preparations may be prepared utilising conventional techniques.

The benefits and parameters of the present invention will now be more fully described with reference to the accompanying examples. It should be understood, however, that the following description is illustrative only and should not be taken in any way as a restriction of the generality of the foregoing description.

EXAMPLE 1

Effects of IGF-I and des(1-3)IGF-I on stomach growth in the growth hormone-deficient lit/lit mouse At 6 weeks of age lit/lit mice were housed individually and weighed on a daily basis, and by 8 weeks of age it had been established that body growth had virtually ceased.

Mice were then randomised into 5 groups according to body weight and sex and were injected daily for 20 days with (a) 120 µl of a sterile solution containing one part of HCl (10 mmol/l) and nine parts of potassium phosphate (50 mmol/l), NaCl (150 mmol/l) and 0.1% human serum albumin at pH 7.4 (diluent), (b) 120 µl of diluent containing 3 µg IGF-I, (c) 120 µl of diluent containing 3 µg des(1–3)IGF-I, (d) 120 µl of diluent containing 30 µg IGF-I, or (e) 120 µl of diluent containing 30 µg des(1–3)IGF-I.

Each dose was administered subcutaneously as two injections, one at 9–10 a.m., the other at 4–5 p.m. The animals were weighed and their lengths measured at 7 day intervals.

On day 21 the animals were killed by an anaesthetic overdose and tissues removed for weighing. The body weights, animal lengths (including tail) and stomach weights are shown in the following Table 1. Values are mans±standard errors with statistical significance from diluent-treated control animals shown as *$P<0.05$; **$P<0.01$. The numbers of animals are given in parentheses.

Since the initial body weights were 10 grams for each group, the daily dose rates were approximately equivalent to 300 µg and 3000 µg of each peptide per kg body weight.

Stomach weights, expressed as a percentage of the diluent group, were 105% and 123% with 300 µg and 3000 µg/kg body weight/day of IGF-I respectively, and 110% and 123% with 300 µg and 3000 µg/kg body weight/day of des(1–3) IGF-I respectively.

EXAMPLE 2

Effects of IGF-I and des(1–3)IGF-I LR$^3$ on gut weights in dexamethasone-treated rats Male Hooded Wistar rats, weighing on average 152 g (range 138–164 g) and maintained in metabolism cages, had Alzet model 2001 osmotic pumps inserted subcutaneously within the scapular region under ether anaesthesia. One pump delivered dexamethasone at 20 micrograms/d and the other either (a) 0.1M acetic acid as diluent;

(b) IGF-I at 111 µg/d;

(c) IGF-I at 278 µg/d;

(d) IGF-I at 695 µg/d;

(e) des(1–3) GF- at 44 µg/d;

(f) des(1–3)IGF-I at 111 µg/d;

(g) des(1–3)IGF-I at 278 µg/d;

(h) LR$^3$ at 44 µg/d;

(i) LR$^3$ at 111 µg/d;

(j) LR$^3$ at 278 µg/d.

Animals were maintained in the metabolism cages for 7 days with daily measurements of body weight, food and nitrogen intake and nitrogen excretion. After this period the animals were killed by exsanguination under anaesthesia and the gastro-intestinal tract from stomach to colon was removed and separated into stomach, duodenum, jejunum plus ileum, cecum and colon. All regions were cleared of food or fecal contents and weighed.

The body weights and the weights of the different regions of the gastrointestinal tract are given as means ±standard errors in Table 2. Statistical significance from the diluent-treated group is shown as *$P<0.05$; $P<0.01$; *$P<0.001$. There were six animals in each group.

The weights of the total gut from stomach through colon is depicted in FIG. 1 as a fraction of total body weight in the format of dose-response curves for IGF-I, des(1–3)IGF-I and LR$^3$.

For a midpoint region of the ileum and the colon a portion was cut longitudinally and scraped to remove the mucosal layer. The weight of this layer was expressed as a percentage of the total mucosa plus muscularis. The protein contents of the same regions of the ileum were measured and expressed as mg per gram wet weight of tissue. These values are given as means±standard errors in Table 3. Statistical significance from the diluent-treated animals was not achieved using ANOVA ($P>0.05$).

This example demonstrates marked increases in the weights of different regions of the gut of dexamethasone-treated rats following the administration OF IGF-I, des(1–3) IGF-I or LR$^3$. The effects are dose dependent and are greater for des(1–3)IGF-I or LR$^3$ at doses equivalent to IGF-I.

The increased growth occurs predominantly through an expansion in the cross-sectional area of the gut because the length of each region is either not increased or increased only slightly.

It is evident from FIG. 1 that the increase in gut weight is proportionally above that occurring for body weight.

Both mucosal and muscularis regions of the jejunum and colon show increased growth because the percent by weight accounted for by the mucosa is not affected by IGF treatment.

Growth occurs by an increase in tissue protein since the percent protein content of the jejunum and colon is not changed by IGF treatment.

EXAMPLE 3

Quantitative histology of the duodenum from rats in Example 2

The mid region of the duodenum from certain animals in Example 1 was fixed in Bouin's fixative, dehydrated, embedded, transverse sections cut and stained with haematoxylin and eosin for quantitative histological analysis. All animals in groups (a), (c), (g) and (j) of Example 2 were processed and measurements of villus height, crypt depth, mucosal area, submucosal area, muscularis external area and total cross-sectional area were obtained. For each duodenum, 30 villus heights, 30 crypt depths and 8 area measurements were averaged to obtain representative values. Means±SEM (N=6) are shown in Table 4.

This example establishes that the growth of the duodenum produced by IGF-I, des(1–3)IGF-I or LR$^3$ at dose rates of 278 µg/d is accompanied by statistically significant ($P<0.01$) increases in cross-sectional area. The increase is predominantly in the mucosal area, although the muscularis layer is also increased. The villi that make up much of the mocusa and play a key role in digestion and absorption, are also increased in height.

EXAMPLE 4

Effects of IGF-I and des(1–3)IGF-I on gut weights in rats treated following partial resection of the jejunum plus ileum Male Sprague Dawley rats, weighing on average 175 g (range 160–193 g) and maintained in metabolism cages, had Alzet model 2001 osmotic pumps inserted as in Example 2. The dose rages of growth factors were 170 µg/d for IGF-I and for des(1–3)IGF-I as well as a higher dose rate of 425 µg IGF-I/d. At the same time as the pumps were inserted subcutaneously, and using tribromethanol in amylene hydrate anaesthesia and aseptic techniques, the jejunum plus ileum was exposed through a mid-line incision. The mid 80% of these parts of the intestine was removed starting 10 cm from the ligament of Treitz and finishing 10 cm from the ileo-cecal valve. The intestine and abdominal cavity were bathed frequently in sterile saline containing penicillin (1000 U/ml). To further guard against possible infection, the animals were injected with 0.6 ml of procaine penicillin before surgery and again 4 days later. The animals were returned to their metabolic cages and allowed free access to food and water. Body weights, food intakes, nitrogen intakes and nitrogen outputs were measured daily.

After 7 days of treatment, the animals were killed by exsanguination under anaesthesia and the gastro-intestinal tract from stomach to colon was removed and separated into stomach, duodenum, residual jejunum plus ileum, colon and cecum. All collected regions of the gut were cleared of food or fecal contents and weighed. The body weights and the weights of the different regions of the gut are given as means±standard errors in Table 5. Statistical significance from the diluent-treated group is shown as *P<0.05; **P<0.01. There were 7 animals in the diluent and des(1-3) IGF-I groups, six in the group with the low dose of IGF-I and five in the group with the high dose of IGF-I.

The example shows that des(1-3)IGF-I and a 2.5 fold higher dose of IGF-I produce pronounced growth effects on the gut. A dose of IGF-I equal to that of des(1-3)IGF-I gave no statistically-significant effects.

The total gut weight less the residual jejunum and ileum, expressed as a percentage of the diluent group, was 113% with 170 µg IGF-I/d, 131% with 425 µg IGF-I/d, and 125% with 170 µg des(1-3)IGF-I/d.

EXAMPLE 5

Figure 2:
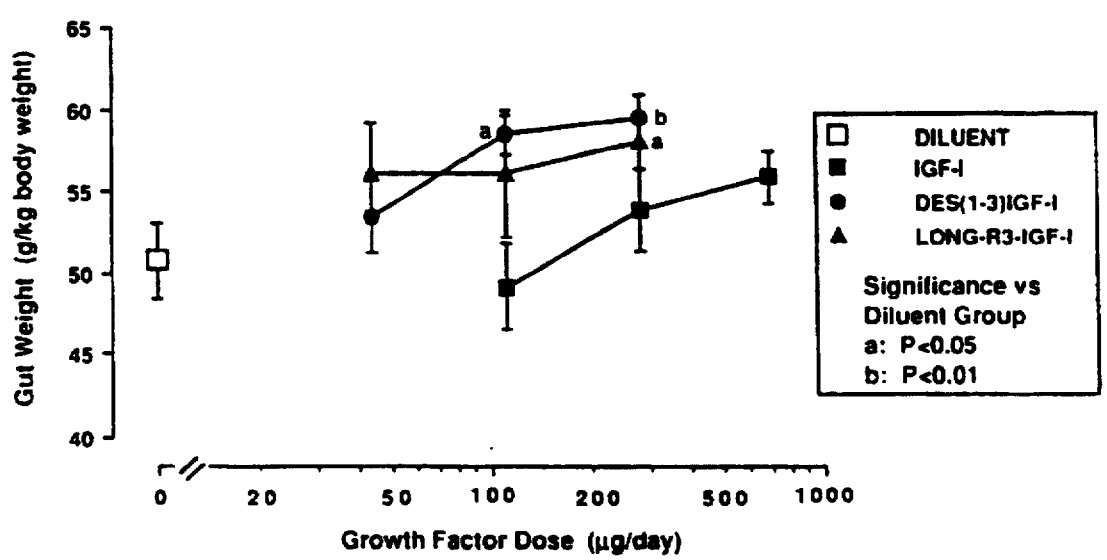
FIG. 2 illustrates the effect on total gut weight (stomach to colon) of diabetic rats treated with IGF's for 7 days. Letters indicate statistical significance (ANOVA) from diluent group: (a) $P<0.05$; (b) $P<0.01$; (c) $P<0.001$.

Effects of IGF-I, des(1-3)IGF-I and MpGH(11)VN/R$^3$IGF-I (LR$^3$) on gut growth in diabetic rats Male Hooded-Wistar rats weighing approximately 150 g were injected with streptozotocin intra-peritoneally at a dose of 70 mg/kg and transferred to metabolic cages. Diabetes was confirmed by blood glucose measurements. After 7 days (average body weight 162 g) the animals were implanted with osmotic pumps in exactly the same way and to deliver exactly the same doses as in Example 1. After 7 days treatment the animals were killed and the weights of the following gut organs measured: stomach, duodenum, ileum plus jejunum and colon. These values are shown in Table 6 and the total gut weights in FIG. 2. Each value is the mean±SEM for six animals. Statistical significance (ANOVA; least significant difference) is shown by *P<0.05, P<0.01, *P<0.001 versus diluent-treated diabetic rats.

These results demonstrate that IGF-I and lower doses of des(1-3)IGF-I or LR$^3$ produce substantial growth effects on the stomach, ileum plus jejunum, colon and total gut weights. Effects on the duodenum are somewhat less.

The response of IGFs in the diabetic rats is especially important since even untreated animals already have heavier gut weights as a result of the hyperphagia associated with this condition. For example the weight of ileum plus jejunum was 5.08±0.29 g in another group of animals in which the diabetes was treated by insulin administration. This is lower than the diluent group in Table 5, notwithstanding the fact that the body weight of the insulin-treated animals was much heavier (231±8 g).

EXAMPLE 6

Effects of IGF-I and des(1-3)IGF-I on gut weights in rats following partial nephrectomy Partial renal failure was produced in Sprague Dawley male rats (95-125 g) by a 2-stage sub-total nephrectomy. This was performed via flank insicions, by ligating terminal branches of the left renal artery to give ischemia of at least half of the left kidney (Day 0), with a right nephrectomy being undertaken one week later, at which time the right jugular vein was also cannulated (Day 7). Partially nephrectomized rats were selected on day 14 for inclusion in the treatment period of the study on the basis of detectable proteinuria, and of increased urine volume and serum urea levels at least twice those of the sham-operated control animals. On Day 16 treatment was commenced by means of mini-osmotic pumps (Alzet Model 2001, Alza Co., Palo Alto, Calif.) which were implanted subcutaneously in the dorsal thoracic region under halothane anesthesia. Nephrectomized rats were randomly allocated to 4 treatment groups: diluent treated 0.1M acetic acid), low dose IGF-I treated (170 µg/d), high dose IGF-I treated (425 µg/d), or des(1-3)IGF-I treated (170 µg/d). The average body weight at time of pump insertion was 193 g. Animals were killed on Day 23 and gut weights measured as in Example 2. These are shown in Table 7. Statistical significance from diluent-treated animals is indicated by *P<0.05, **P<0.01.

This example demonstrates that gut weights are increased by 7 days treatment with IGF-I or des(1-3)IGF-I in rats that are compromised by partial nephrectomy.

Finally, it is to be understood that various other modifications and/or alterations may be made without departing from the spirit of the present invention as outlined herein.

TABLE 1

Growth effects of IGF-I and des(1-3)IGF-I over a 20-day treatment period of lit/lit mice

| Treatment Group | | Body Weight (g) | Animal Length (mm) | Stomach Weight (mg) |
|---|---|---|---|---|
| Diluent (8) | | 10.20 ± 0.19 | 124 ± 2 | 64.3 ± 3.0 |
| IGF-I, | 3 µg/d (8) | 10.75 ± 0.28 | 127 ± 1 | 67.8 ± 2.1 |
| | 30 µg/d (6) | 11.25 ± 0.41 | 132 ± 1* | 79.0 ± 3.0** |
| des(1-3)IGF-I, | 3 µg/d (8) | 10.76 ± 0.31 | 127 ± 2 | 70.6 ± 2.5 |
| | 30 µg/d (6) | 11.33 ± 0.42 | 132 ± 1 | 79.3 ± 4.4** |

TABLE 2

Gut weights (g), lengths (cm) and body weights (g) of dexamethasone-treated rats also treated with IGF-I, des(1-3)IGF-I or LR$^3$

| Treatment | | Body Weight | Stomach Weight | Duodenum Weight | Duodenum Length |
|---|---|---|---|---|---|
| Diluent | | 131 ± 3 | 0.87 ± 0.03 | 0.50 ± 0.02 | 7.2 ± 0.4 |
| IGF-I, | 111 µg/d | 130 ± 4 | 0.93 ± 0.03* | 0.55 ± 0.03 | 6.9 ± 0.3 |
| | 278 µg/d | 143 ± 4* | 1.09 ± 0.02*** | 0.70 ± 0.02*** | 7.6 ± 0.2 |
| | 695 µg/d | 158 ± 2*** | 1.17 ± 0.02*** | 0.84 ± 0.02*** | 8.0 ± 0.2* |
| des(1-3)IGF-I, | 44 µg/d | 135 ± 3 | 0.98 ± 0.02** | 0.63 ± 0.03** | 7.6 ± 0.3 |
| | 111 µg/d | 144 ± 5* | 1.06 ± 0.02*** | 0.68 ± 0.02*** | 7.6 ± 0.2 |
| | 278 µg/d | 151 ± 2*** | 1.14 ± 0.02*** | 0.86 ± 0.03*** | 8.7 ± 0.3*** |
| LR$^3$ | 44 µg/d | 135 ± 1 | 0.95 ± 0.01* | 0.61 ± 0.02** | 7.3 ± 0.3 |
| | 111 µg/d | 140 ± 4 | 1.07 ± 0.02*** | 0.75 ± 0.03*** | 7.6 ± 0.4 |
| | 278 µg/d | 150 ± 3*** | 1.16 ± 0.02*** | 0.86 ± 0.03*** | 8.3 ± 0.2** |

| Ileum + Jejunum Weight | Ileum + Jejunum Length | Colon Weight | Colon Length |
|---|---|---|---|
| 3.07 ± 0.22 | 70.8 ± 4.1 | 0.68 ± 0.05 | 11.0 ± 0.4 |
| 3.60 ± 0.19 | 71.8 ± 2.6 | 0.64 ± 0.02 | 12.0 ± 0.3 |
| 4.30 ± 0.21*** | 71.7 ± 3.1 | 0.92 ± 0.04*** | 13.3 ± 0.6 |
| 5.22 ± 0.23*** | 86.1 ± 3.6 | 0.93 ± 0.05*** | 12.7 ± 0.6 |
| 3.80 ± 0.25* | 72.1 ± 3.5 | 0.72 ± 0.05 | 11.3 ± 0.8 |
| 4.44 ± 0.24*** | 71.8 ± 2.6 | 0.86 ± 0.04** | 13.4 ± 0.5 |
| 5.09 ± 0.21*** | 73.0 ± 4.1 | 0.91 ± 0.04*** | 11.3 ± 0.8 |
| 3.93 ± 0.24** | 72.4 ± 3.8 | 0.75 ± 0.03 | 12.3 ± 0.2 |
| 4.67 ± 0.18*** | 75.8 ± 3.3 | 0.89 ± 0.05** | 12.5 ± 0.8 |
| 5.20 ± 0.33*** | 79.5 ± 4.1 | 0.98 ± 0.05*** | 12.9 ± 0.6 |

TABLE 3

Fractional weights and protein contents of the jejunum in the mucosal layers in the jejunum and in the colon dexamethasone-treated rats treated with IGFs

| Treatment | | Jejunum Mucosa (% of total) | Jejunum Mucosa Protein (mg/g weight) | Jejunum Muscularis Protein (mg/g weight) | Colon Mucosa (% of total) |
|---|---|---|---|---|---|
| Diluent | | 55.1 ± 3.3 | 124 ± 5 | 169 ± 4 | 30.5 ± 2.5 |
| IGF-I, | 111 µg/d | 58.8 ± 2.2 | 117 ± 6 | 151 ± 4 | 29.6 ± 1.7 |
| | 278 µg/d | 62.7 ± 1.5 | 135 ± 5 | 161 ± 5 | 31.7 ± 1.7 |
| | 695 µg/d | 61.1 ± 2.8 | 136 ± 5 | 159 ± 2 | 28.8 ± 1.2 |
| des(1-3)IGF-I, | 44 µg/d | 53.3 ± 3.9 | 134 ± 5 | 161 ± 5 | 31.1 ± 1.7 |
| | 111 µg/d | 59.6 ± 2.3 | 140 ± 5 | 162 ± 4 | 27.5 ± 2.2 |
| | 278 µg/d | 55.3 ± 3.6 | 140 ± 4 | 154 ± 6 | 32.5 ± 2.5 |
| LR$^3$, | 44 µg/d | 56.8 ± 4.2 | 119 ± 10 | 147 ± 4 | 30.2 ± 2.8 |
| | 111 µg/d | 60.7 ± 3.3 | 139 ± 4 | 168 ± 6 | 29.6 ± 2.1 |
| | 278 µg/d | 54.2 ± 3.2 | 135 ± 6 | 159 ± 5 | 30.6 ± 2.2 |

TABLE 4

Sections from rats treated with IGF-I des(1-3)IGF-I, LR$^3$ or diluent

| Measurement | Diluent | IGF-I | des(1-3)IGF-I | LR$^3$ |
|---|---|---|---|---|
| Villus height (mm) | 0.65 ± 0.02 | 0.76 ± 0.03 | 0.73 ± 0.03 | 0.84 ± 0.031*** |
| Crypt depth (mm) | 0.20 ± 0.01 | 0.23 ± 0.01 | 0.23 ± 0.00 | 0.23 ± 0.01 |
| Villus:crypt ratio | 3.3 ± 0.2 | 3.4 ± 0.2 | 3.3 ± 0.1 | 3.7 ± 0.2 |
| Mucosal area (mm$^2$) | 5.67 ± 0.44 | 7.72 ± 0.56** | 8.03 ± 0.58** | 8.29 ± 0.56*** |
| Sub-mucosal area (mm$^2$) | 0.42 ± 0.04 | 0.51 ± 0.04 | 0.52 ± 0.03 | 0.51 ± 0.04 |
| Musc. externa area (mm$^2$) | 1.20 ± 0.15 | 1.51 ± 0.05* | 1.54 ± 0.06** | 1.41 ± 0.12 |
| Total area (mm$^2$) | 7.29 ± 0.61 | 9.74 ± 0.59** | 10.10 ± 0.62** | 10.21 ± 0.66** |

*P < 0.05, P < 0.01, *P < 0.001 versus diluent

TABLE 5

| Duodenum weight (mg) | Diluent | IGF-I 170 µg/d | IGF-I 425 µg/d | des(1-3)IGF-I 170 µg/d |
|---|---|---|---|---|
| Body weight (g) | 171.6 | 173.4 | 190.9 | 184.1 |
| | ± 4.5 | ± 5.9 | ± 4.2 | ± 5.6 |
| Stomach weight (mg) | 980 | 1089 | 1236** | 1136* |
| | ± 75 | ± 47 | ± 26 | ± 52 |
| Duodenum weight (mg) | 1067 | 1179 | 1572** | 1542** |
| | ± 75 | ± 88 | ± 81 | ± 102 |
| Residual Jejunum + Ileum weight (mg) | 1984 | 2217 | 2288 | 2259 |
| | ± 118 | ± 244 | ± 60 | ± 150 |
| Colon weight (g) | 1067 | 1305 | 1330 | 1250 |
| | ± 162 | ± 164 | ± 65 | ± 127 |
| Total gut weight less residual jejunum & ileum (g) | 4.28 | 4.83 | 5.59** | 5.37** |
| | ± 0.27 | ± 0.34 | ± 0.13 | ± 0.24 |

TABLE 6

Gut weights (g) of diabetic rats and body weights (g)

| | | Body Weight | Stomach | Duodenum | Ileum + Jejunum | Colon |
|---|---|---|---|---|---|---|
| Diluent | | 172 ± 6 | 1.01 ± 0.04 | 0.72 ± 0.09 | 6.10 ± 0.49 | 0.95 ± 0.02 |
| IGF-I, | 111 µg/d | 186 ± 4 | 1.13 ± 0.04 | 0.74 ± o.08 | 6.21 ± 0.37 | 1.05 ± 0.07 |
| | 278 µg/d | 198 ± 8* | 1.19 ± 0.06* | 0.91 ± 0.05 | 7.41 ± 0.32* | 1.09 ± 0.05 |
| | 695 µg/d | 210 ± 8*** | 1.44 ± 0.08*** | 0.94 ± 0.06* | 8.17 ± 0.32*** | 1.18 ± 0.05** |
| des(1-3)IGF-I, | 44 µg/d | 185 ± 6 | 1.23 ± 0.051* | 0.82 ± 0.11 | 6.83 ± 0.38 | 1.02 ± 0.05 |
| | 111 µg/d | 194 ± 7* | 1.27 ± 0.06** | 0.89 ± 0.07 | 7.97 ± 0.20** | 1.16 ± 0.08** |
| | 278 µg/d | 212 ± 8*** | 1.49 ± 0.07*** | 1.02 ± 0.09*** | 8.69 ± 0.40*** | 1.41 ± 0.03*** |
| LR$^3$ | 44 µg/d | 190 ± 7 | 1.14 ± 0.06 | 0.85 ± 0.07 | 7.58 ± 0.48* | 1.05 ± 0.04 |
| | 111 µg/d | 204 ± 6** | 1.38 ± 0.04*** | 0.88 ± 0.11 | 7.83 ± 0.53** | 1.25 ± 0.07*** |
| | 278 µg/d | 213 ± 8*** | 1.48 ± 0.08*** | 0.91 ± 0.06 | 8.47 ± 0.46*** | 1.50 ± 0.04*** |

TABLE 7

Gut weights (g) in partially-nephrectomised rats treated with IGF-I or des(1-3)IGF-I

| Treatment | | Stomach | Duodenum | Ileum + Jejunum | Colon | Total |
|---|---|---|---|---|---|---|
| Diluent | | 1.08 ± 0.04 | 0.51 ± 0.02 | 3.78 ± 0.19 | 0.83 ± 0.03 | 6.21 ± 0.22 |
| IGF-1, | 170 µg/d | 1.19 ± 0.03 | 0.63 ± 0.03* | 4.70 ± 0.27** | 0.97 ± 0.03* | 7.50 ± 0.30** |
| | 425 µg/d | 1.25 ± 0.06* | 0.75 ± 0.07** | 5.11 ± 0.22** | 1.05 ± 0.07** | 8.16 ± 0.27** |
| des(1-3)IGF-I | 170 µg/d | 1.16 ± 0.06 | 0.66 ± 0.03* | 4.48 ± 0.15* | 0.95 ± 0.06 | 7.24 ± 0.10** |

We claim:

1. A method of treatment in a mammalian subject of a disorder in gut function, wherein the disorder in gut function results in the subject having a lesser amount of gut tissue than required for normal digestion or absorption, which method comprises administering to the subject an effective amount of mammalian IGF-1, des(1-3)IGF-I, or $LR^3$.

2. The method of claim 1, wherein the disorder in gut function is short gut syndrome, chronic ulcerative gut disease, inflammatory gut disease, or necrotizing enterocolitis.

3. The method of claim 2, wherein the inflammatory gut disease is colitis or Crohn's disease.

4. The method of claim 1, wherein the treatment increases gut weight relative to the weight of the subject.

5. The method of claim 4, wherein the increase in gut weight is due to an increase in the weight of one or more of stomach, duodenum, jejunum, ileum, or colon.

6. The method of claim 4, wherein the increase in gut weight is due to an increase in cross-sectional area, muscularis layer, mucosal area, or villus height in gut tissue.

7. The method of claim 1, wherein the gut tissue affected by the disorder is stomach, small intestine, duodenum, jejunum, ileum, cecum, colon, or combinations thereof.

8. The method according to claim 1 wherein the mammalian IGF-I, des(1–3) IGF-I or $LR^3$ is administered intravenously, subcutaneously, intramuscularly or enterally.

9. The method according to claim 1 wherein the mammalian IGF-I, des(1–3) IGF-I or $LR^3$ is administered in an amount of from 10 to 5000 microgram/kg body weight/day for a period of 1 to 60 days.

10. The method according to claim 1, wherein the mammalian IGF-I is human IGF-I.

11. A method of treatment in a mammalian subject of inflammatory gut disease, wherein the subject has a lesser amount of gut tissue than required for normal digestion or absorption, which method comprises administering to the subject an effective amount of mammalian IGF-1, des(1–3) IGF-I, or $LR^3$.

12. A method of treatment in a mammalian subject of chronic ulcerative gut disease, wherein the subject has a lesser amount of gut tissue than required for normal digestion or absorption, which method comprises administering to the subject an effective amount of mammalian IGF-1, des(1–3)IGF-I, or $LR^3$.

13. A method of treatment in a mammalian subject of short gut syndrome, wherein the subject has a lesser amount of gut tissue than required for normal digestion or absorption, which method comprises administering to the subject an effective amount of mammalian IGF-1, des(1–3) IGF-I, or $LR^3$.

14. A method of treatment in a mammalian subject of necrotizing enterocolitis, wherein the subject has a lesser amount of gut tissue than required for normal digestion or absorption, which method comprises administering to the subject an effective amount of mammalian IGF-1, des(1–3) IGF-I, or $LR^3$.

* * * * *

UNITED STATES PATENT AND TRADEMARK OFFICE
CERTIFICATE OF CORRECTION

PATENT NO. : 5,679,771

DATED : OCTOBER 21, 1997

INVENTOR(S) : BALLARD ET AL.

It is certified that error appears in the above-identified patent and that said Letters Patent is hereby corrected as shown below:

Col. 1, line 42: "251" should read —261—

Col. 9, Table 4: "0.84 ± 0.031*" should read —0.84 ± 0.03*—

Col. 11, Table 6: "1.23 ± 0.051*" should read —1.23 ± 0.05**—

Signed and Sealed this

Thirteenth Day of July, 1999

Attest:

Q. TODD DICKINSON

Attesting Officer

Acting Commissioner of Patents and Trademarks